(12) United States Patent
Dryer et al.

(10) Patent No.: US 7,642,062 B2
(45) Date of Patent: Jan. 5, 2010

(54) COMPOSITIONS AND METHODS OF THEIR USE FOR IMPROVING THE CONDITION AND APPEARANCE OF SKIN

(75) Inventors: Laurence Dryer, Butler, NJ (US); Sherrie R. Tafuri, Nanuet, NY (US); Dmitri Ptchelintsev, Jersey City, NJ (US)

(73) Assignee: Avon Products Inc., New York, NY (US)

( * ) Notice: Subject to any disclaimer, the term of this patent is extended or adjusted under 35 U.S.C. 154(b) by 160 days.

(21) Appl. No.: 11/647,648

(22) Filed: Dec. 29, 2006

(65) Prior Publication Data

US 2008/0160109 A1 Jul. 3, 2008

(51) Int. Cl.
*G01N 33/543* (2006.01)
*G01N 33/53* (2006.01)

(52) U.S. Cl. .................. 435/7.21; 435/7.1; 436/501; 436/518

(58) Field of Classification Search .................. None
See application file for complete search history.

(56) References Cited

U.S. PATENT DOCUMENTS

| | | | |
|---|---|---|---|
| 4,379,454 | A | 4/1983 | Campbell et al. |
| 4,820,724 | A | 4/1989 | Nimni |
| 4,956,171 | A | 9/1990 | Chang |
| 5,146,846 | A | 9/1992 | Lee et al. |
| 5,223,262 | A | 6/1993 | Kim et al. |
| 5,770,222 | A | 6/1998 | Unger et al. |
| 5,834,513 | A | 11/1998 | Ptchelintsev et al. |
| 5,847,003 | A | 12/1998 | Ptchelintsev et al. |
| 6,096,327 | A | 8/2000 | Lezdey et al. |
| 6,764,826 | B2 | 7/2004 | Yeh et al. |
| 2005/0031572 | A1 | 2/2005 | Gallinat et al. |
| 2005/0221334 | A1 | 10/2005 | Benson |

FOREIGN PATENT DOCUMENTS

| | | | |
|---|---|---|---|
| WO | WO 01/66067 A1 | | 9/2001 |
| WO | WO01/68804 | * | 9/2001 |
| WO | WO 03/079816 A1 | | 10/2003 |
| WO | 2004/014404 A1 | | 2/2004 |
| WO | WO 2004/014958 A1 | | 2/2004 |

OTHER PUBLICATIONS

Faloon, William. "Eating Food Cooked at High Temperature Accelerates Aging," LE Magazine, May 2003, http://www.lef.org, Accessed Sep. 17, 2008.*
C. Franceschi, et al. Inflamm-aging: An Evolutionary Perspective on Immunosenescence Ann NY Acad Sci, 908: 244-254 (2000).

* cited by examiner

Primary Examiner—Lisa V Cook
(74) Attorney, Agent, or Firm—Joan M. McGillycuddy; Charles J. Zeller; Anthony M. Santini

(57) ABSTRACT

The present invention relates to compositions and methods for treating, preventing and improving the condition and aesthetic appearance of skin, particularly, treating, preventing, ameliorating, reducing and/or eliminating fine lines and/or wrinkles of skin, where the compositions include natural plant constituents, or synthetic equivalents thereof, which inhibit or decrease expression of C-reactive protein expression, production or secretion, thereby reducing, inhibiting, or ameliorating dermatological signs of aging. The compositions of the invention may be topically applied to the skin, or are delivered by directed means to a site in need thereof, in an amount effective in improving the condition and aesthetic appearance of skin.

4 Claims, No Drawings

COMPOSITIONS AND METHODS OF THEIR USE FOR IMPROVING THE CONDITION AND APPEARANCE OF SKIN

FIELD OF THE INVENTION

This invention generally relates to cosmetic, dermatological, and pharmaceutical compositions and their use, and more particularly to cosmetic compositions and to their use in improving the condition and appearance of skin.

BACKGROUND OF THE INVENTION

There is an increasing demand in the cosmetics industry to develop products that may be applied topically to the skin that improve the condition and appearance of skin. Consumers are interested in mitigating or delaying the dermatological signs of chronologically or hormonally-aged or photo-aged skin, such as fine lines, wrinkles, drying, and sagging skin, and other conditions due to a progressive degradation of the skin matrix. During the aging process, the complexion of the skin, i.e., the color and appearance of the skin, deteriorates slowly from aging and/or exposure to sunlight. Numerous cosmetic and medical treatments have been developed in an attempt to treat aging or aged skin. Such cosmetics or treatments commonly contain organic acids as their active ingredients or components. These actives are frequently associated with consumer discomfort, such as burning, itching, and redness.

C-Reactive Protein (CRP) is a member of a class of acute phase reactants which increases during inflammatory processes, and thereby acts as a marker of inflammation. Measuring and monitoring C-reactive protein values are useful in determining disease progression or the effectiveness of treatments. Homo sapiens C-reactive protein (CRP) is a pentameric protein that has also been found to play a role in heart disease and is an indicator of risk for hypertension, recurring coronary events, and cardiovascular disease (mRNA: Accession No. NM_00567; gene: Accession No. AF442818; mapped to chromosome 1 region q21 to q25; protein: Accession No. AAL48218). Human CRP is composed of five 206 amino acid subunits non-covalently bound, each having a molecular weight of 23,017 daltons (Mullenix and Mortensen, *Mol. Immunol.*, 31(8):615-22, 1994). Human CRP is normally present in trace amounts in serum, at very low levels, e.g., 0.8-3 g/mL. However, during infection and inflammation, human CRP levels can increase by 1,000-fold in response to specific cytokines.

There remains a general need in the cosmetics industry for products that retard or counter the aging effects on the skin, and more specifically for products that produce such effects without undesirable side effects. In particular, there remains a need for topically applied cosmetic compositions that have anti-aging, anti-inflammatory, and skin texture benefits using natural plant materials as active components.

The genus *Humulus* of the *Cannabaceae* family, have been employed for a variety of purposes. The hop (*Humulus*) is a small genus of flowering plants, native to the temperate Northern Hemisphere. The female flowers, commonly called hops, are commonly used as flavoring and stabilizers during the process of brewing beer. Humulene and lupulene are medically active ingredients in hops. Dried female buds having a high methylbutenol content, are mildly sedating on the central nervous system. Hops may be used in the treatment for insomnia, stress, anxiety. Isolated from hops, Xanthohumol, has been shown to have anti-cancer properties. Xanthohumol has been shown to be toxic to human breast cancer, colon and ovarian cancer cells, as well as has some activity against prostate cancer. In addition to its anti-cancer effects, hops has antibacterial characteristics which stimulate gastric juice production. There are several species (and varieties) belonging to this genus, including: *H. aculeatus, H. americanus, H. cordifolius, H. japonicus* (*H. japonicus* var. *variegatus*), *H. lupulus* (*H. lupulus* subsp. *americanus, H. lupulus* var. *cordifolius, H. lupulus* var. *lupuloides, H. lupulus* var. *lupulus, H. lupulus* var. *neomexicanus, H. lupulus* var. *pubescens*), *H. neomexicanus, H. scandens* (*H. scandens* var. *varigatus*), and *H. yunnanensis*.

The *Humulus scandens, Humulus japonicus, Humulus lupulus,* and *Humulus yunnanensis* species in the genus *Humulus* are all herbaceous vines with hooked climbing hairs and twine clockwise up. These species generally are dioecious, i.e., sexually distinct plants; however, individual monoecious plants, i.e., hermaphroditic, have been identified. Although male and female plants are easily distinguishable during flowering, there are no other morphological differences with which to identify the sex of a plant.

*Humulus japonicus*, also synonymous with *Humulus scandens*, is commonly known as Asian Hop. *Humulus japonicus* is a dioecious annual originating in Eastern Asia. It generally has leaves with 5-7 lobes, long internodes, and extremely strong hooked climbing hairs. It may be used as an ornamental primarily for hedges, but its aggressive nature and particularly strong climbing hairs make it unpleasant to handle and a potentially invasive weed. Because its female inflorescence is smaller than the cone of *H. lupulus* and there are few glands on either its leaves or cones, there is little value for *H. japonicus* in the brewing industry.

*Humulus lupulus* is a perennial that grows again each spring from the rhizomes of an underground rootstock. In the wild, *H. lupulus* spreads through underground rhizomes and by seed. *H. lupulus* has been separated into five taxonomic varieties based primarily on leaf characteristics, including but not limited to, pubescence, leaf hairs, leaf lobes and the number of glands.

Brewers have determined that European hops are milder and more aromatic than those from North America. European-type hops are less pubescent, have fewer glands, and have heart-shaped leaves with few lobes. Native North American hops are generally heavily pubescent and have deeply lobed leaves with five or seven lobes. North American hops have been described as having high resin content and as rich with glands and "buttery" to touch.

*Humulus yunnanensis* is a dioecious perennial with leaves that are less lobed and cones larger than those of *H. japonicus*. *H. yunnanensis* is distinguishable by the stiffness of the climbing hairs, pubescent leaf surfaces, small leaf glands, distribution of the trichomes, and large pollen grains. *H. yunnanensis* has only a few glands on the bracteoles of the cone and similar to *H. japonicus*, has no value for brewing.

It would be desirable to have a composition, preferably topical, comprising a natural plant material to improve the aesthetic appearance of skin. It would also be desirable to have an effective treatment and preventative for the dermatological signs of aging, including inflammation. Therefore, safe, effective and new compositions to treat, prevent, reduce, inhibit, and/or improve the dermatological signs of aging, would be advantageous for the formulation of treatments and products for the skin. As described herein, novel and beneficial methods and compositions, as well as their mode of action, for the treatment of wrinkles and the like, as well as for personal care products for the skin, are provided by the present invention.

SUMMARY OF THE INVENTION

It is an object of the present invention to provide a composition that delivers an effective level of an active component from a natural plant material that inhibits and decreases the production and/or secretion of C-reactive protein.

It is another object of the present invention to provide a composition having a natural plant material, blends of natural plant materials, or synthetic equivalents, in a cosmetically, dermatologically, physiologically, or pharmaceutically acceptable vehicle.

It is a further object of the present invention to provide a composition having a natural plant material, component therefrom, or synthetic equivalent, that results in decreased or inhibited expression of C-reactive protein thereby reducing dermatological signs of chronologically or hormonally-aged or photo-aged skin, such as fine lines, wrinkles, and sagging skin, where the composition is a cosmetic, dermatological, or pharmaceutical product.

It is yet another embodiment of the invention to provide a method of treating, preventing, and/or ameliorating the appearance of fine lines and/or wrinkles, comprising applying to skin a composition having a natural plant material, combinations of natural plant materials, or synthetic equivalents thereof, in an amount effective to prevent, ameliorate and/or reduce dermatological signs of chronologically or hormonally-aged or photo-aged skin, such as fine lines, wrinkles, and sagging skin.

It is still a further object of the present invention to provide a composition having one or more of the following natural plant materials: *H. scandens, H. japonicus, H. lupulus*, and *H. yunnanensis*, in an amount effective to treat, prevent, control, ameliorate, inhibit, and/or reduce dermatological signs of chronologically or hormonally-aged or photo-aged skin, such as fine lines, wrinkles, and sagging skin, in order to improve the aesthetic appearance of skin by inhibiting C-reactive protein secretion or production.

Yet another object of the invention provides a method of detecting CRP-associated inflammation and aging skin by reacting a skin sample with a probe and detecting the presence of the probe, where the probe detects a CRP and detection of the probe indicates CRP-associated inflammation and a risk of CRP-associated progression of aging skin.

A further embodiment of the invention relates to a method of monitoring a skin sample by treating the skin sample with a test composition forming a treated skin sample, reacting the treated skin sample with a probe, reacting a control skin sample with a probe, and comparing the control skin sample to the treated skin sample for the presence of the probe, where the presence of the probe identifies the presence of CRP, thereby monitoring the treatment of a skin sample.

These and other objects and advantages of the present invention, and equivalents thereof, are achieved by cosmetic compositions having a natural plant ingredient or blends thereof, and methods of use of such compositions for topical application in order to improve the aesthetic appearance of skin.

DETAILED DESCRIPTION OF THE INVENTION

In accordance with the foregoing objectives and others detailed herein, the invention overcomes deficiencies associated with the prior art by providing compositions comprising at least one C-reactive protein (CRP) inhibitor which improves the aesthetic appearance or condition of skin resulting from the chronological aging process. The composition and methods thereof, once applied to a biological surface or synthetic biological surface, rejuvenates or enhances the surfaces by providing a variety of anti-inflammatory, anti-aging, and skin texture benefits that are both visible and invisible. CRP may also be used as a biomarker for CRP-associated inflammation and chronological aging.

In yet another embodiment, the topical compositions having at least one active ingredient that acts as a CRP inhibitor may be used to treat, prevent, ameliorate, and/or reduce dermatological signs of chronologically aging, which represent the structural, functional, and metabolic changes in the skin that parallel the aging and degenerative changes in other body organs, or photo-aged skin, which is a separate process and largely involves damage to the collagen and elastin fibers in the skin, as fine lines, wrinkles, and sagging skin, in order to improve the condition and aesthetic appearance of skin.

Another embodiment of the invention relates to compositions having an active component derived from a natural plant material or combinations thereof, where a "natural plant material" includes an ingredient, component, constituent, or extract derived from the natural plant material, or synthetic equivalent thereof. The active component inhibits the expression, production, or secretion of CRP, and upon application to biological surfaces, improves the aesthetic appearance or condition of the skin by decreasing the natural aging process, inflammation, and chronic and cumulative damage to biological surfaces. Improvements in the aesthetic appearance of biological surfaces, e.g., skin, may be preferably achieved by topical application of these compositions to the skin on a daily basis.

A further embodiment of the invention relates to the novel use of natural plant materials in the genus *Humulus* and family *Cannabaceae*, including but not limited to, *H. scandens, H. japonicus, H. lupulus, H. yunnanensis* plants, or similar plants, alone or in combination, in a topical cosmetic composition for application on the face, body, and/or hair in order to improve the condition and aesthetic appearance of skin affected by the natural aging process, where chronic and cumulative damage to the skin matrix and inflammation normally occur. It is also contemplated that other natural plant materials may work equally as well if they inhibit, reduce, or decrease production, secretion, or expression of CRP associated with dermatological signs of aging and/or their underlying causative factors. In another embodiment of the invention, any natural plant material or active ingredient that acts as a CRP inhibitor may be useful in inhibiting, reducing, treating, preventing, or reversing the aging process or results therefrom.

For purposes of the invention, the natural plant material may be in any form including, but not limited to, the whole plant, a dried plant, a ground plant, or parts thereof, including but not limited to, seeds, needles, leaves, roots, bark, cones, stems, rhizomes, callus cells, protoplasts, organs and organ systems, and meristems, or components and/or constituents found in, or isolated from, the natural plant material, and/or portions of the plant, or extracts derived either directly or synthetically from the plant, or any combinations thereof. A preferred natural plant material is in the form of an extract derived from the natural plant material; however, one embodiment of the invention utilizes a synthetic equivalent of the natural plant material of interest for use in improving the aesthetic appearance or condition of skin resulting from the natural aging process. It is to be understood that "natural plant material" also includes an ingredient, component, constituent, or extract derived from the natural plant material, or synthetic equivalent thereof.

One embodiment of the composition of the invention, comprises at least one natural plant extract which inhibits the expression, production, or secretion of CRP when applied to a biological surface, such as keratinous tissue. The biological surface may be any surface to which cosmetics, personal care products, dermatological, and pharmaceutical compositions are typically applied, including but not limited to skin, lips, hair, nails, and the like. The composition that is applied to biological surfaces improves the aesthetic appearance of skin by decreasing the natural aging process, inflammation, and chronic and cumulative damage to biological surfaces.

The skin is made up of multiple layers of cells that are constantly going through self shedding and regeneration once every 30 days in repeated cycles. The layers may be broadly divided into two sections—the top epidermis and the underlying dermis. Histological studies of the skin show that a wrinkle is formed following a series of major cellular changes. During the early phase of aging (from age 35-45), there is a gradual and progressive slowing of cellular turnover and regeneration. This results in the skin getting thinner. Skin ages as a result of time and of cell divisions which may be reversible or irreversible. Aging skin may be induced or accelerated by environmental factors, such as but not limited to sun exposure, pollutants, toxins, and smoking.

Symptoms of chronological aging include: dry and thin skin, fine wrinkles, abnormal blood vessels, age spots, and benign and/or malignant skin tumors. Young skin renews itself more frequently than older skin. The top layers thereby lose more moisture due to the aging process, and older skin has a drier and more dehydrated appearance. Diminished production of collagen leads to fine wrinkles initially observed around the eyes (commonly known as "crow's feet"), forehead, and other sun-exposed areas. More pronounced effects include furrows at the site of facial expression lines and sagging folds over the eyelids, neck, jaw, and arms. Within the many small, delicate blood vessels supplying nutrients to the skin, abnormalities develop. This is particularly conspicuous over the nose and cheeks. Age spots are pigmentations that surfaced as a result of a deregulation of pigment cells in sun-exposed areas. Hyper- and hypo-pigmentation are also a result of the aging process.

While genetics play a significant role, the number of wrinkles present is highly dependent on the amount of sun exposure and other environmental factors. The lines in a "lived-in face," especially for those who spend a considerable amount of time outdoors, is a consequence in part of oxidative damage due to overexposure to ultraviolet (UV) sunlight—both UVA (responsible for tanning, wrinkling, and melanoma) and UVB (responsible for sunburn and basal and squamous cell carcinoma). UV light may further damage skin by increasing the production of proteolytic enzymes that break down collagen, the connective tissue located beneath the dermis.

Reduced nutrition to the epidermis from aging is one factor that causes cellular exhaustion and weakness. Without proper nutrition to the epidermis, cellular metabolism of the epidermal cell is slowed. Furthermore, the transportation of certain unwanted byproducts of cellular metabolism such as free radicals are reduced. The accumulation of such free radicals within the cell may lead to undesirable mutational damages in the cell and ultimately cancer.

Embodiments of the invention relate to the discovery that natural plant materials having a C-reactive protein (CRP) inhibitor in a composition or formulation diminish skin lines and wrinkles, as well as relieves sagging, or other conditions due to aging. "Inflammaging" is a term that correlates inflammatory changes with age-related diseases. More specifically, inflammaging is the up-regulation of the inflammatory response that is age-dependent (Franceschi C, Bonafe M, Valensin S, Olivieri F, De Luca M, Ottaviani E, De Benedictis G. Inflamm-aging. "An evolutionary perspective on immunosenescence." *Ann N Y Acad Sci.;* 908:208-218, 2000). Without wishing to be bound by theory, CRP inflammation has been associated with aging skin, reflected by wrinkles and sagging, which are accelerated by chronic inflammation. Thus, by inhibiting or decreasing the production, secretion, or stimulation of CRP in skin, one may improve the condition and aesthetic appearance of skin.

In yet another embodiment of the invention, methods of using the composition having a CRP inhibitor useful for improving the condition and aesthetic appearance of skin, particularly matured or maturing skin, by any one of the following means: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof In another embodiment, the present invention encompasses a method of improving the condition and aesthetic appearance of skin, thereby reducing inflammation and other signs of aging, comprising applying to an affected area of skin, a composition containing a natural plant material, or extract therefrom, selected from: *H. scandens, H. japonicus, H. lupulus, H. yunnanensis*, variations thereof, or combinations thereof; or any natural plant material, or extract therefrom, that inhibits expression of C-reactive protein production and secretion.

One embodiment of the invention relates to methods of applying an effective amount of a natural plant material, or extract derived therefrom, to inhibit expression of C-reactive protein production and secretion to an affected area of the skin. The composition is preferably topical and applied once daily and remains on the affected area of the skin, where the affected area of the skin includes, but is not limited to, the face, neck, legs and thighs, scalp, and overall body.

Another embodiment of the present invention relates to a method of improving the condition and aesthetic appearance of skin and comprises applying to the skin, or introducing via a directed mode of delivery, a composition including one or more natural plant materials, or components derived therefrom, in an amount effective to improve the aesthetic appearance of conditions related to skin, where the natural plant material inhibits expression of C-reactive protein production and secretion.

In a specific embodiment, the component is in an extract of one or more of the natural plant materials described in a pharmaceutically, physiologically, cosmetically, and dermatologically-acceptable vehicle, diluent, or carrier, where the composition is topically applied to an affected area of skin and left to remain on the affected area in an amount effective for treatment for the dermatological signs of aging and improving the condition and aesthetic appearance of skin.

In a further embodiment, the natural plant material as used herein, also includes "synthetic" extracts, i.e. various combinations of known the natural plant material components and/or constituents that are combined to substantially mimic the composition and/or activity of the natural plant material. Such synthetic extracts are included in the term "natural plant material extract." Most preferably, the synthetic extracts have substantially the same number of active components as a natural plant material. The correspondence of the numerical incidence of actives between the synthetic extracts and the natural plant material may also be described in terms of "percent commonality."

Another embodiment relates to a synthetic extract having about 50% or more commonality to the chemical composition of a natural plant material. For example, the synthetic extract has about 50% or more of the active components found in the natural plant material. The chemical composition of the synthetic extract may have about 70% or more commonality to the chemical composition of the natural plant material. A synthetic extract may have about 90% or more commonality to the chemical composition of the natural plant material.

For use in the compositions of the invention, the natural plant material and/or active components are derived directly from the natural plant material, including the entire plant, its seeds, needles, leaves, roots, bark, cones, stems, rhizomes, callus cells, protoplasts, organs and organ systems, and meristems. The components may be in a pure form, a semi-pure form, or unpurified form. The natural plant material in the form of an extract may be obtained by extracting either the entire plant, or various parts thereof, with 80% ethanol.

Briefly, the extraction method involves washing and extracting the plant material using water, followed by concentrating and filtering. The solid matter is removed and liquid-liquid butanol/water purification steps occur. Butanol (lipophilic impurities, and residual pesticides are removed. The produce is dried and results in a dry purified extract.

In one embodiment, the extraction method may involve a) pretreating the plant material, which involves washing, then cutting or crushing; b) heat concentrating the cut or crushed plant material from step a); c) extracting the concentrate from step b) with water; d) concentrating the concentrate from step c); e) filtrating the concentrate of step d) and removing solid matter; f) purifying with liquid-liquid butanol/water; g) removing butanol, lipophilic impurities, residual pesticides, and the like; h) drying with or without pressure; and i) resulting in the dry and purified plant material extract. One skilled in the art understands that a variety of extraction methods may be used including for example, WO 03/079816; WO 04/014404; and WO 04/014958.

Additionally, an organic solvent extraction method which involves washing and extracting the plant material using an organic solvent may be used to extract the plant material. Non-limiting examples of organic solvents include methanol, ethanol, isopropanol, dichloromethane, chloroform, hexane, xylene, and petroleum ether. An extracting machine may be used for organic solvent extraction as is well known in the field.

Organic solvent extraction involves collecting the raw materials from the plant that contain the desired constituent (s), such as seeds, needles, leaves, roots, bark, cones, stems, rhizomes, callus cells, protoplasts, organs and organ systems, and meristems. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time between about 1-8 hours is suitable, and more preferably is between about 2-6 hours, and most preferably is between about 3-5 hours. The temperature of extraction is between about 30° C.-90° C., preferably between about 40° C.-70° C., and more preferably between about 50° C.-60° C. The collected extract is then fine-filtered to remove debris, and may be used directly, or is concentrated, for example, by distilling the solvent or by other conventional processing, where the extract may also be provided as a dry powder.

Similarly, aqueous-organic solvent extraction involves initially collecting raw materials from a plant containing the desired alkaloid(s), such as seeds, needles, leaves, roots, bark, cones, stems, rhizomes, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract actives from an aqueous phase to an organic phase. Non-limiting examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Different plants containing different constituents may be mixed and extracted together. This process of mixed extraction may preferably be used for extracting those plants containing constituents having similar solubility in the solvent used for extraction, such as ethanol. The mixture of extracts may be concentrated and stored in an appropriate solvent.

In another embodiment, the composition may have an extract derived from a natural plant material or active ingredient that inhibits CRP production, secretion, or expression in an amount from about 0.0001% to about 50%, preferably from about 0.001% to about 20%, more preferably from about 0.01% to about 5%, and most preferably from about 0.3% to about 1%, based on the total weight of the composition, where the composition is useful in improving the condition and aesthetic appearance of skin.

The active ingredient or component of a cosmetic, dermatological or pharmaceutical composition is derived from any one, or combinations thereof, of plants including but not limited to: *H. scandens, H. japonicus, H. lupullus, H. yunnanensis*, any natural plant material, or synthetic equivalent thereof, that inhibits or decreases CRP expression levels, production, or secretion when the composition is applied to a biological surface. The CRP inhibitor active ingredient which is associated with dermatological signs of chronologically or hormonally-aged or photo-aged skin, such as fine lines, wrinkles, and sagging skin, is useful in improving the condition and aesthetic appearance of skin when applied, preferably topically in a daily manner to biological surfaces including skin. Without wishing to be bound by theory, the natural plant extracts and active ingredients therein and thereof, which are CRP inhibitors, exert their effects through a mechanism of action involving the inflammatory and immune systems associated with aging. CRP found in skin is a sign of cumulative and chronic damage to the skin matrix that causes skin matrix degradation. Topical application of the composition having the CRP inhibitor facilitates the targeted delivery of the active components without the requirement of an injection or the expertise of a health practitioner.

The active ingredient of the present invention, includes at least one CRP inhibitor, but may include non-limiting examples of active ingredients useful in treating, preventing, arresting, ameliorating, reducing or diminishing, medical and/or cosmetic conditions associated with aging and inflammation of the skin. Such conditions, as used herein, commonly include, but are not limited to, dermatological aging (chronological aging, hormonal aging and/or actinic aging), dermatitis, skin and hair fragility, hirsutism, rosacea, skin blemishes, sensitive skin, hyperpigmentation or hypopigmentation, thinning skin, roughness, keratosis, skin atrophy, wrinkles, lines, hyperplasia, fibrosis, and any combinations thereof. The active components of the present invention may also be useful in enhancing the general health, vitality, condition, and aesthetic appearance of the skin.

Topical compositions having the aforementioned active components derived from a natural plant material or synthetic equivalent thereof, where the active components decrease or inhibit CRP expression, production, or secretion improve the condition, cosmetic, and/or aesthetic appearance of skin, particularly of aging and/or inflamed skin.

A further embodiment of the invention encompasses the use of CRP as a biomarker for compounds which improve the condition and appearance of skin associated with dermatological signs of aging, such as fine lines, wrinkles, and sagging skin. If expression levels of such biomarkers are decreased in the presence of a composition, where the composition may be used in a cosmetic, dermatological, or pharmaceutical composition of the invention for improving the condition and appearance of inflamed and aging skin. Preferably the active ingredient of the composition comprises a natural plant material, or synthetic equivalent thereof that inhibits CRP expression, production, or secretion. A variety of methods for measuring CRP protein and nucleic acid levels in cells that have been exposed to one or more test samples may be performed. A probe may be used to detect the CRP biomarker. As defined herein, a probe refers to a protein that specifically binds CRP or a fragment thereof, and a nucleic acid or oligonucleotide that forms a hybrid structure with a sequence in a target region of CRP due to complementarily of at least one sequence in the probe with a sequence in the CRP target region.

Suitable methods include detection and evaluation of gene activation or expression of, for example, DNA, RNA, or mRNA. As non-limiting examples, polymerase chain reaction (PCR) assays (e.g., RT-PCR), Northern blotting, in situ hybridization, and other assays as known and practiced in the art may be employed to quantify RNA in cells being assayed for tolerance to a particular treatment (see, e.g., J. O'Connell, 2002, *RT-PCR Protocols*, Humana Press, Totowa, N.J.; R. Rapley and D. L. Manning, 1998, *RNA Isolation and Characterization Protocols*, Humana Press; R. Rapley, 2000, *Nucleic Acid Protocols Handbook*, Humana Press; all of which are herein incorporated by reference). In accordance with such assays, if levels of at least one nucleic acid biomarker is decreased in the presence of one or more test samples, this is indicative that the substance(s) will decrease, reduce, or ameliorate the dermatological signs of aging.

Nucleic acids may hybridize to each other when at least one strand of nucleic acid anneals to another nucleic acid strand under defined stringency conditions. As is well known in the art, stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two nucleic acids contain substantially complementary sequences; depending on the stringency of hybridization; however, mismatches may be tolerated. The appropriate stringency for hybridizing nucleic acids depends on the length of the nucleic acids and the degree of complementarity, variables well known in the art.

Furthermore, in addition to nucleic acid probes, protein probes specific to the C-reactive protein may also be useful in detecting the presence of CRP-associated inflammation and age progression in biological surfaces, including skin. For example, in Western blots, antibodies that specifically bind to CRP, or fragments of CRP, may be used to determine the presence or absence of CRP in control and test samples. The presence of CRP may be determined through a variety of tests that are well known to and commonly practiced by those skilled in the art.

These assays are useful in monitoring the affects after daily application over a period of time of the inventive composition to a biological surface, e.g., skin. If expression levels of the CRP biomarker are decreased in the presence of one or more test samples, this is indicative that the test sample(s) will decrease, reduce, or ameliorate the signs of dermatological aging, especially fine lines, wrinkles, and sagging skin, thereby improving the condition and aesthetic appearance of aging skin.

In accordance with the invention, compositions comprising CRP inhibitors including components from the natural plant material *H. scandens, H. japonicus, H. lupulus, H. yunnanensis*, or combinations thereof, may be useful in topically applied formulations, anti-oxidants, anti-inflammatories, sunscreens, cosmetics, including makeup, formulations for reducing dermatological signs of aging, including wrinkles, fine lines, and sagging skin, topicals, skin penetration enhancers, and the like. Also in accordance with this invention, the active ingredient being a CRP inhibitor, for example in a natural plant material, and additional constituents in a composition, may be formulated in a variety of product forms. The compositions may be prepared in targeted delivery systems, e.g. creams, lotions, masks, gels, toners, serums, transdermal patches, and the like, particularly for topical administration. Targeted delivery and/or penetration enhancement may also be achieved by iontophoresis.

The present invention further provides the compositions comprising the natural plant materials preferably for topical administration or for targeted delivery without inducing significant irritation. The inventive compositions are suitable for all skin types, such as sensitive, normal, dry, or oily, preferably sensitive to dry skin, as well as mature skin. In particular embodiments, the compositions may be suitable for dry skin. The compositions are applied to the skin for a period of time sufficient to improve the condition or aesthetic appearance of skin. The compositions may be applied topically once, twice, or more daily to biological surfaces, including but not limited to skin, lips, and hair. The daily application may be applied for a period of one week, two weeks, four weeks, or more. The preferred composition or formulation comprising a CRP inhibitor may be applied and left on the affected area once daily.

The topical compositions may be formulated into liposomes which may comprise other additives or substances, and/or which may be modified to more specifically reach or remain at a site following administration. The compositions of embodiments of the present invention yield improvements to the conditions and aesthetic appearance of skin by treating at least one of the previously described conditions, or combinations thereof.

As will be appreciated by the practitioner, cosmetic treatments comprising compositions containing natural plant materials, including extracts, components, and/or constituents of the invention may be carried out, for example, by topically applying the cosmetic composition as described herein according to the routine technique for administering such compositions. The topical cosmetic, dermatological, or pharmaceutical composition preferably is applied once daily for a period of at least one week, but may include a period of about 2, 4, 8, or 12 weeks. The cosmetic composition is preferably applied to the face and neck, but may be applied to any area of skin in need of aesthetic improvement, where the cosmetic composition remains on the affected area of skin, and preferably not removed or rinsed off the skin. Routine and commonly practiced techniques encompass the application of creams, lotions, gels, masks, sera, ointments, patches, makeup, makeup-removing milks, sunscreen compositions, or the like, to the skin. Preferably the cosmetic composition is a topical leave on formulation, where spraying as a form of application is also envisioned.

Another embodiment of the invention encompasses compositions comprising a cosmetically, dermatologically, or pharmaceutically acceptable formulation which is suitable for contact with living mammalican tissue, including human tissue, or synthetic equivalents thereof, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include but are not limited to, for example, an emulsion, a cream, a balm, a gloss, a lotion, a mask, a serum, a toner, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, perilla oil or perilla seed oil (WO 01/66067 to a "Method of Treating a Skin Condition," incorporated herewith) and the like, as well as other botanicals such as aloe, chamomile, and the like, and as further described below.

Also, embraced by the invention are transdermal modes of delivery, such as patches and the like, with or without a suitable penetration enhancers. The methods and compositions embodied by the invention provide a means by which the natural plant material components may be effectively administered in a transdermal system. Accordingly, a transdermal means of delivering a composition or formulation (often with a penetration enhancing composition) to the skin is that of the transdermal patch or a similar device as known and described in the art. Examples of such devices are disclosed in U.S. Pat. Nos. 5,146,846; 5,223,262; 4,820,724; 4,379,454; and 4,956,171, all of which are incorporated herein by reference and such descriptions are not meant to be limiting. The transdermal mode of storing and delivering the compositions onto the skin, including hair, and forming the active composition is convenient and well-suited for the purposes of an embodiment of the present invention. In a preferred method, the application is through a sustained release vehicle, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

The natural plant material component(s) of the present invention are preferably contained in a cosmetically, dematologically, physiologically, and pharmaceutically acceptable vehicle, medium, diluent or carrier, for use in treating, reducing, ameliorating, or preventing conditions associated with aging and inflammation in particular CRP-associated inflammation and aging of biological surfaces.

In an embodiment embracing topical application, the compositions of this invention comprise a medium (vehicle, diluent or carrier) that is compatible with mammalian skin, including hair. The compositions can be formulated as an aqueous phase, an oil phase, alcohol, or aqueous/alcohol-based solutions, ointments, creams, lotions, gels, a wax-in-water emulsion, or water-in-oil, oil-in-water, of water-oil-water triple emulsions having the appearance of a cream or gel, microemulsions, or aerosols.

The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate cosmetic form, the ingredients contained therein, as well as the method for preparing it, on the basis of the knowledge that the skilled artisan possesses.

In one embodiment, the composition may include an aqueous phase which may contain water or a mixture of water and at least one hydrophilic organic solvent in particular an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 weight % to about 99.99 weight %, based upon the total weight of the composition.

Yet another embodiment when the composition of the invention is in the form of an emulsion, the composition may also optionally comprise a surfactant, preferably in an amount of from about 0.1 weight % to about 30 weight %, and in particular, from about 1 weight % to about 20 weight %, based upon the total weight of the composition.

In a further embodiment of the invention, the composition may also comprise a thickening polymer such as an amphiphilic polyurethane, a polyacrylic homopolymer or copolymer, a polyester, or a hydrocarbon-based resin.

One embodiment of the invention further relates to a composition of the invention which may also comprise an oil phase containing oil soluble or oil dispersible ingredients that are liquid at room temperature (25° C.) and/or oily or waxy substances that are solid at room temperature, such as waxes, semi-solids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polydimethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of about 0 weight % to about 90 weight %, preferably from about 1 weight % to about 80 weight % by weight of the oil phase.

The oil phase of the composition of the invention may also comprise one or more cosmetically acceptable organic solvents. These solvents are present in an amount of about 0 weight % to about 60 weight %, preferably about 1 weight % to about 30 weight %, based on the total weight of the composition, and may be selected from the group consisting of lipophilic organic solvents, amphiphilic organic solvents and mixtures thereof. Suitable solvents which may be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetics field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetics field to achieve their intended purpose, and range typically from about 0.01 weight % to about 20 weight %, based upon the total weight of the composition. The nature of these ingredients and their amounts must be compatible with the production of the compositions of the invention.

The composition of the invention may also comprise an additional particulate phase, typically present in an amount of about 0 weight % to about 30 weight %, based upon the total weight of the composition, preferably from about 0.05 weight % to about 20 weight %, and which can comprise pigments and/or pearlescent agents and/or fillers used in cosmetic compositions. Suitable inorganic pigments include, but are not limited to, titanium oxide, zirconium oxide and cerium oxide, as well as zinc oxide, iron oxide, chromium oxide and ferric blue. Suitable organic pigments include, but barium, strontium, calcium, and aluminum lakes and carbon black. Suitable pearlescent agents include mica coated with titanium oxide, with iron oxide, or with natural pigment.

Fillers are normally present in an amount of about 0 weight % to about 30 weight %, based on the total weight of the composition, preferably about 0.5 weight % to about 15 weight %. Suitable fillers include talc, silica, zinc stearate, mica, kaolin, nylon (in particular orgasol) powder, polyethylene powder, Teflon®, starch, boron nitride, copolymer microspheres such as Expancel® (Nobel Industrie; Sweden), Polytrap® (Dow Corning, Inc.; Midland, Mich.), and silicone resin microbeads (Tospearl®; GE Toshiba Silicones; Japan).

The oil phase of the compositions of the invention may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present invention may contain from about 0 weight % to about 20 weight % waxes, based upon the total weight of the composition.

The gums are generally high molecular weight polydimethylsiloxanes (PDMSs), cellulose gums or polysaccharides, and the semi-solid materials are generally hydrocarbon-based compounds, such as, but not limited to, lanolins and derivatives thereof, or alternatively PDMSs. The compositions of the present invention may contain from about 0 weight % to about 20 weight % gums, based upon the total weight of the composition, typically from about 0.1 weight % to about 10 weight %.

More particularly, the compositions for topical application can be in the form of a protective care composition for the skin, preferably for the face, the neck, the hands, the feet, or other areas of the body. Non-limiting examples include day creams or lotions, night creams or lotions, salves, sunscreen creams, fluid lotions, oils, ointments, gels, masks, body milks, makeup (a foundation), artificial tanning compositions, depilatories, emulsifiers, patches, or a solid which is poured or cast as a stick or a dish, for example.

Another particular embodiment of the present invention is directed to the delivery of the described compositions comprising a natural plant material by targeted delivery systems, for example, liposomes, microspheres (see, e.g., U.S. Pat. No. 5,770,222 to Unger et al., incorporated herein by reference), and the like, so that the natural plant material compositions and/or active constituents may more readily reach and affect the dermal-epidermal junction layer of the area where the composition is topically applied, e.g., face or neck, or other affected areas of the skin.

In another embodiment, the topical compositions of the present invention may also include one or more of the following: a skin penetration enhancer, an emollient, a skin plumper, an optical diffuser, a sunscreen, an exfoliation promoter, and an antioxidant. Details with respect to these and other suitable cosmetic ingredients can be found in the *International Cosmetic Ingredient Dictionary (ICID) and Handbook*, 10th Edition (2004), published by the Cosmetic, Toiletry, and Fragrance Association (CTFA), at pp. 2177-2299, which is herein incorporated by reference in its entirety.

An emollient provides the functional benefits of enhancing skin smoothness, reducing the appearance of fine lines and coarse wrinkles, and moisturizing. Non-limiting examples include isopropyl myristate, petrolatum, isopropyl lanolate, silicones (e.g., methicone, dimethicone), oils, mineral oils, fatty acid esters, or any mixtures thereof. The emollient is preferably present from about 0.1 weight % to about 50 weight % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 weight % to about 20 weight % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 weight % to about 20 weight % of the total weight of the composition.

A sunscreen protects the skin from damaging ultraviolet rays. In an illustrative embodiment of the invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 weight % to about 30 weight % of the total weight of the composition. The addition of a sunscreen may protect the skin from ultraviolet radiation.

The compositions of the invention having sunscreen bring about additional improvements to the aesthetic appearance of skin, including at least one of the following: minimizes sunburning, minimizes tanning, and reduces redness.

In an embodiment of the invention, compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof. (See also, ICID at p. 2205).

When an embodiment of the invention includes an exfoliation promoter, the composition has about 0.1 weight % to 30 weight %, preferably about 1 weight % to about 15weight % and more preferably about 1 wt % to about 10 wt %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 wt % to about 10 wt %, and more preferably from about 0.01 wt % to about 5 wt %, of the total weight of the composition. (See also, ICID at p. 2184).

In an embodiment of the invention, the composition may also have one or more of the following cosmetic and pharmaceutical active agents, excipients, ingredients, or adjuvants: anesthetics, antibiotics, e.g., erythromycins and tetracyclines, salicylic acids, anti-allergenics, antifungals, antiseptics, anti-irritants, anti-inflammatory agents, antimicrobials, analgesics, nitric oxide synthase inhibitors, insect repellents, self-tanning agents, skin penetration enhancers, skin cooling agents, chelating agents, colorants including dyes, lakes and pigments that may be untreated or chemically surface treated to improve wetability or some other property, demulcents, emollients, emulsifiers, fragrances, humectants, lubricants, skin protectants, moisturizers, pH adjusters, preservatives, stabilizers, surfactants, thickeners, film formers, plasticizers, viscosity modifiers, vitamins, or any mixtures thereof. The amounts of these various substances are those that are conventionally used in the cosmetic or pharmaceutical fields to achieve their intended purposes, for example, they may constitute from about 0.01% to 20% of the total weight of the composition.

Non-limiting examples of active agents for formulating into the compositions of the invention include those reagents having an effect on the treatment of wrinkles and/or fine lines, in addition to the actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic, acid, 5-n-octylsalicylic acid, 5-n-heptyloxysalicylic acid, 4-n- heptyloxysalicylic acid and 2-hydroxy-3-methylbenzoic acid or alkoxy derivatives thereof, such as 2-hydroxy-3-methyoxybenzoic acid.

Emulsifiers are typically present in the compositions of the invention in an amount of about 0.01 weight % to 30 weight %, by weight and preferably from about 0.1 weight % to 30 weight % by weight relative to the total weight of the composition. However, not all compositions will necessarily include emulsifiers. (See e.g., ICID at p. 2276-2285).

Non-limiting examples of suitable thickening agents include xanthan gum, hydroxypropyl cellulose, hydroxyethyl cellulose, carbomer, gum acacia, Sepigel 305 (available from Seppic Co., France), and clays such as magnesium aluminum silicate. (See, e.g., ICID at p. 2293-2299).

The topical compositions of the present invention may include, and their utility can be enhanced by one or more humectants, such as ureas, pyrrolidone carboxylic acids, amino acids, sodium hyaluronates, certain polyols and other compounds with hygroscopic properties. (See ICID at p. 2244).

The general activity and mildness to skin of the present topical compositions can also be enhanced by neutralization to pH about 3.5 to about 7.0, most preferably from pH about 3.7 to about 5.6. This neutralization is preferably accomplished with one or more of ammonium hydroxide, potassium hydroxide, sodium hydroxide, arginine or other amino acids, and/or triethanolamine.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The natural plant materials, or extracts therefrom, of the present invention are preferably contained in a cosmetically or dematologically acceptable vehicle, medium, diluent or carrier. The topical composition comprising the natural plant materials may be further formulated according to procedures known in the art to provide cosmetic compositions such as emulsions, gels, creams, lotions, masks, toners, serums, oils, water-in-oil, oil-in-water, water-oil-water triple emulsions having the appearance of a cream or gel, microemulsions, ointments, pastes, sticks, cakes, pencils, aerosol, and essences, as well as other topical cosmetic vehicles. It is also contemplated that topical compositions of the present invention can be incorporated into delivery systems such as liposomes and topical patches, tapes, and sprays.

In addition, the compositions may be in the form of vesicular dispersions containing ionic and/or nonionic lipids, as described above. Dosage units suitable for such compositions are formulated according to the conventional knowledge and techniques used in the art.

In a further embodiment of the invention, the compositions for topical application may be in the form of a protective care composition for the skin, preferably for the face, the neck, the hands, the feet, or other areas of the body. Non-limiting examples include day creams or lotions, night creams or lotions, sunscreen creams, lotions, or oils, body milks, makeup (a foundation), artificial tanning compositions, depilatories, and patches.

EXAMPLES

The following examples describe specific aspects of the invention to illustrate the invention and provide a description of the present methods for those skilled in the art. The examples should not be construed as limiting the invention, as the examples merely provide specific methodology useful in the understanding and practice of the invention and its various aspects.

Example 1

A plant extract of the present invention may be extracted from natural raw materials by using the methods of aqueous-organic solvent extraction as is well known in the art. One such extraction process is set forth below. In another embodiment, plant extracts may be commercially obtained, for example from Indena S.p.A. (Milan, Italy).

The following describes a suitable method of preparing a natural plant extract useful for preparing a topical composition of the present invention.

An extract was obtained by extracting the whole plant or parts thereof, such as for example, the aerial (i.e., above ground) part of the *Humulus scandens* plant using an butanol extraction scheme as generally known in the art. Briefly, the *Humulus scandens* plant or parts thereof (could be first manually ground into small particle sizes resulting in a powder) were extracted with water. After concentrating and filtering, the solid matter was removed. The remaining concentrate was further purified and, butanol, and any impurities, for example, lipophilic impurities and residual pesticides, were removed. The total concentrated extract was then dried, for example by lyophilization, resulting in a dry purified extract of *H. scandens*.

Example 2

Any composition comprising ingredients normally used in formulating cosmetic foundations with C-reactive protein inhibitors, natural plant extracts having similar properties, or synthetic equivalents thereof may be used (see, e.g., Table 1).

TABLE 1

| INGREDIENTS | % |
|---|---|
| Water | q.s. 100% |
| Thickener | 1.00 |
| Preservative | 0.65 |
| Butylene glycol | 13.00 |
| Pigment | 16.00 |
| Sunscreen | 2.00 |
| Emulsifier | 0.70 |
| Polymer | 13.00 |
| Other active ingredients | 4.70 |
| *Humulus scandens* | 0.3 |

Example 3

Biopsy Assay

Normal human subjects completed a 3-week clinical study in which formulas containing the active ingredients were applied daily on the forearm under semi-occlusive conditions, after which a punch biopsy was taken at each site, the biopsy fixed in formalin, and processed for immunohistochemistry with a C-Reactive Protein (CRP) antibody (R&D Systems; Minneapolis, Minn.).

Twenty-one (21) normal human subjects were tested on a their forearm, free of topical drugs, cosmetics, and damage to the skin, for 3 weeks (3 consecutive rounds of 5×24 hour patches under semi-occlusion; i.e., 5 days a week for 3 wks) with 8 different active ingredients. The application dose applied to the skin was 2 mg/cm$^2$. After the three weeks application clinical study, a 2 millimeter punch biopsy was obtained from each site to which a different application was tested. Two additional biopsies were taken from each subject, one from an untreated site and another from a vehicle-treated site for controls.

Normal subjects, specifically human, were in good health, age 30-65, not pregnant or planning to get pregnant or nursing, free of skin diseases, diabetes, renal diseases, heart condition, or immunological disorders. The subjects' skin photodamage was mild to moderate as determined visually. No subject was under systemic corticosteroids, Accutane™, immunosuppressive drugs, or systemic birth control.

Potentially misleading areas, such as sites of inflammation (needle site, bruises revealed by histology, etc.) or biopsy edges were avoided. Also, vehicle effects were taken into account, where vehicle effects are any effect due to the solvent (rather than the ingredient) used to dissolve the ingredient in order for application to the skin. Each punch biopsy was fixed in 4% paraformaldehyde. The biopsies were embedded in paraffin and sectioned (5 μm thickness), and stained after rehydration. Sections were stained for C-reactive protein (R&D Systems; polyclonal anti C-reactive protein).

Histological evaluation of the stained biopsies was carried out by two trained experts in a semi-blind directional difference paradigm. Controls were identified but not the formulas containing the different active ingredients. The stained biopsies were separated into three categories: No improvement, Slight improvement, or Marked improvement. Improvement consisted of a reduction in the amount and intensity of staining revealed by the antibody.

The number of panelists showing improvement was determined and a percentage of success derived. Of the 21 human subjects, 52% showed improvement for in the presence of *Humulus scandens:* 4 subjects showed marked improvement, 6 slight improvement, 9 showed no improvement and 2 could not be evaluated. The seven other tested ingredients failed. On the basis of these numbers as well as the observed magnitude of the non-quantitative response by the experts, only *Humulus scandens* was determined to elicit an improvement in a majority of subjects.

The content of all patents, patent applications, published articles, abstracts, books, reference manuals and abstracts, as cited herein are hereby incorporated by reference in their entireties to more fully describe the state of the art to which the invention pertains.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A method of detecting CRP-associated inflammation and aging skin comprising:
    a) reacting a normal skin sample with a probe; and
    b) detecting the presence of the probe,
wherein the probe detects a C-reactive protein and detection of the probe indicates CRP-associated inflammation and a risk of CRP-associated progression of aging skin.

2. A method of monitoring a normal skin sample, comprising:
    a) treating a normal skin sample with a test composition forming a treated skin sample;
    b) reacting the treated skin sample with a probe;
    c) reacting a control skin sample with a probe; and
    d) comparing the control skin sample to the treated skin sample for the presence of the probe,
wherein the presence of the probe identifies the presence of C-reactive protein, thereby monitoring the treatment of a normal skin sample.

3. The method of claim 2, wherein the probe is a nucleic acid that is specific far CRP.

4. The method of claim 2, wherein the probe is a protein that is specific for CRP.

* * * * *